United States Patent [19]

Lu et al.

[11] Patent Number: 5,338,773
[45] Date of Patent: Aug. 16, 1994

[54] DENTAL COMPOSITION AND METHOD

[75] Inventors: Kewang Lu; Chin-Teh Huang, both of Dover; Paul Hammesfahr, Wyoming, all of Del.

[73] Assignee: Dentsply Research & Development Corp., Milford, Del.

[21] Appl. No.: 49,221

[22] Filed: Apr. 19, 1993

[51] Int. Cl.$^5$ .................. A61K 6/08; C07C 321/00; C07C 322/00; C07C 315/00
[52] U.S. Cl. .................... 523/116; 523/118; 524/436; 524/437; 560/10; 560/11; 560/18; 560/48; 560/56; 560/64; 562/427; 562/429; 562/432; 562/467; 562/473; 562/457
[58] Field of Search ............... 523/116, 118; 524/436, 524/437; 560/10, 11, 18, 48, 56, 64; 562/427, 429, 432, 467, 473, 457

[56] References Cited

U.S. PATENT DOCUMENTS

| | | | |
|---|---|---|---|
| 3,234,181 | 2/1966 | Olivier | 260/47 |
| 3,407,176 | 10/1968 | Lonerini | 260/47 |
| 3,422,061 | 1/1969 | Gall | 260/47 |
| 3,424,718 | 1/1969 | Angelo | 260/47 |
| 3,959,350 | 5/1976 | Rogers | 260/47 |
| 4,322,207 | 3/1982 | Madsen | 433/216 |
| 4,324,591 | 4/1982 | Beede et al. | 106/85 |
| 4,336,175 | 6/1982 | Gibbs | 524/726 |
| 4,372,836 | 2/1983 | Schmitt et al. | 204/159.23 |
| 4,401,773 | 8/1983 | Smyth | 523/106 |
| 4,457,818 | 7/1984 | Denyer et al. | 204/159.19 |
| 4,459,193 | 7/1984 | Ratcliffe et al. | 204/159.23 |
| 4,492,777 | 1/1985 | Denton, Jr. et al. | 523/115 |
| 4,514,527 | 4/1985 | Bowen | 523/115 |
| 4,521,550 | 6/1985 | Bowen | 523/116 |
| 4,525,256 | 6/1985 | Martin | 204/159.18 |
| 4,588,756 | 5/1986 | Bowen | 523/116 |
| 4,602,076 | 7/1986 | Ratcliffe et al. | 522/7 |
| 4,612,361 | 9/1986 | Peters | 528/185 |
| 4,657,941 | 4/1987 | Blackwell et al. | 522/14 |
| 4,659,751 | 4/1987 | Bowen | 523/116 |
| 4,680,373 | 7/1987 | Gallager et al. | 528/185 |
| 4,719,149 | 1/1988 | Aasen et al. | 428/473 |
| 4,794,157 | 12/1988 | Berdahl et al. | 528/208 |
| 4,797,431 | 1/1989 | Billington et al. | 523/116 |
| 4,806,381 | 2/1989 | Engelbrecht et al. | 427/2 |
| 4,814,362 | 3/1989 | Billington et al. | 523/117 |
| 4,816,495 | 3/1989 | Blackwell et al. | 522/14 |
| 4,861,808 | 8/1989 | Billington et al. | 523/116 |
| 4,864,015 | 9/1989 | Cella et al. | 528/352 |
| 4,872,936 | 10/1989 | Engelbrecht | 156/307.3 |
| 4,880,660 | 11/1989 | Aasen et al. | 427/2 |
| 4,918,136 | 4/1990 | Kawaguchi et al. | 524/751 |
| 4,964,911 | 10/1990 | Ibsen et al. | 106/35 |
| 4,966,934 | 10/1990 | Huang et al. | 524/315 |
| 4,985,198 | 1/1991 | Hirasawa et al. | 560/130 |
| 5,055,497 | 10/1991 | Okada et al. | 523/116 |
| 5,063,257 | 11/1991 | Akahane et al. | 523/116 |
| 5,079,277 | 1/1992 | Wilson et al. | 523/116 |
| 5,130,347 | 7/1992 | Mitra | 522/149 |
| 5,133,957 | 7/1992 | Suh et al. | 424/49 |
| 5,154,762 | 10/1992 | Metra et al. | 106/35 |
| 5,171,763 | 12/1992 | Ohno et al. | 523/116 |
| 5,241,081 | 8/1993 | Müller et al. | 549/232 |

FOREIGN PATENT DOCUMENTS

| | | |
|---|---|---|
| 873935 | 6/1971 | Canada . |
| 934085 | 9/1973 | Canada . |
| 968741 | 6/1975 | Canada . |
| 969299 | 6/1975 | Canada . |

(List continued on next page.)

*Primary Examiner*—Paul R. Michl
*Assistant Examiner*—LaVonda DeWitt
*Attorney, Agent, or Firm*—Dale R. Lovercheck; Edward J. Hanson, Jr.

[57] ABSTRACT

The invention provides dental cement compositions and methods of using them for binding hard tooth material, metal and ceramic. The cement compositions include polymerizable acid reactive ethylenically unsaturated monomers, and a source of cations reactive therewith, to further crosslink the resulting polymer. The cements have superior adhesion to tooth without separately acid etching dentin or enamel. Compositions of are useful as dental luting cements, liners, bases and restoratives.

20 Claims, No Drawings

FOREIGN PATENT DOCUMENTS

| | | |
|---|---|---|
| 983190 | 2/1976 | Canada . |
| 1018294 | 9/1977 | Canada . |
| 1020687 | 11/1977 | Canada . |
| 1028441 | 3/1978 | Canada . |
| 1117242 | 1/1982 | Canada . |
| 1131388 | 9/1982 | Canada . |
| 1136796 | 11/1982 | Canada . |
| 1154895 | 10/1983 | Canada . |
| 1159984 | 1/1984 | Canada . |
| 1164124 | 3/1984 | Canada . |
| 1176787 | 10/1984 | Canada . |
| 1216982 | 1/1987 | Canada . |
| 1243796 | 10/1988 | Canada . |
| 1244177 | 11/1988 | Canada . |
| 1259149 | 9/1989 | Canada . |
| 1261992 | 9/1989 | Canada . |
| 1262791 | 11/1989 | Canada . |
| 1262981 | 11/1989 | Canada . |
| 1269790 | 5/1990 | Canada . |
| 2009471 | 8/1990 | Canada . |
| 2011438 | 9/1990 | Canada . |
| 2038695 | 3/1991 | Canada . |
| 2051333 | 9/1991 | Canada . |
| 2000789A | 1/1979 | European Pat. Off. . |
| 2156347A | 10/1985 | European Pat. Off. . |
| 0241277 | 10/1987 | European Pat. Off. . |
| 2202221A | 9/1988 | European Pat. Off. . |
| 0325038 | 7/1989 | European Pat. Off. . |
| 0335645 | 10/1989 | European Pat. Off. . |
| 0470446A1 | 2/1992 | European Pat. Off. . |

DENTAL COMPOSITION AND METHOD

The invention relates to dental cement compositions and methods of use thereof to bind hard tooth material, metal and ceramic. The invention provides cement compositions including polymerizable acid reactive ethylenically unsaturated monomers, and a source of cations reactive therewith, to provide further crosslinking in the resulting polymer. The invention provides cements with superior adhesion to dentin, enamel and dentin without the need for separate steps of acid etching dental enamel to adhere to enamel, cement, and superstructure. Compositions of the invention are useful as dental luting cements, liners, bases and restoratives. The compositions of the invention are hydrolytically stable. The heterogeneous multi-phase dental cements disclosed herein include liquid and solids, and show improved mechanical strength. They provide advantages, for example, improved bond strength to tooth and are less sensitive the effects of moisture during the setting reaction.

Prior art zinc oxide/phosphoric acid combinations, known as zinc phosphate cements, are not adhesive to metals, enamel or dentin. Zinc oxide and polyacrylic acid combinations are known as zinc polycarboxylate cements. They are relatively weak and soluble. Glass ionomers are described by A. Wilson in U.S. Pat. Nos. 5,079,277 and 4,758,612. Prior art glass ionomer compositions are combinations of a polyalkenoic acid polymer such as polyacrylic acid and an elutable glass which provides a source of cations to react with the polyacrylic acid. Prior art glass ionomers are brittle and weak in high stress applications and set poorly in the presence of moisture unless protected from water. Prior art pit and fissure materials include polymerizable hydrophobic resins with essentially no adhesion to tooth. They are adhered by infiltrating micromechanical undercuts produced by acid etching. They harden in-situ to protect the tooth from colonization by bacteria in order to reduce caries, but because they are difficult to use they are not universally employed to achieve this valuable result. They require the tooth be cleaned, acid etched, washed, dried and isolated by rubber dam to maintain dryness, to avoid contamination by saliva, and achieve suitable results. The procedure is thus uncomfortable for the patient and laborious for the dentist. The present invention provides pit and fissure sealant compositions which are applied to tooth without a separate acid etching step.

Olivier in U.S. Pat. No. 3,234,181 discloses melt-fabricable end-capped aromatic polyimides.

Lonerini in U.S. Pat. No. 3,407,176 discloses polyamide-acids and polyimide from a mixture of dianhydrides.

Gall in U.S. Pat. No. 3,422,061 discloses coalesceable polyimide powders from a polycarboxylic aromatic dianhydride and phenylene diamine.

Angelo in U.S. Pat. No. 3,424,718 discloses copolymers of aromatic tetracarboxylic acids with at least two organic diamines.

Rogers in U.S. Pat. No. 3,959,350 discloses melt-fusible linear polyimide of 2,2-bis(3,4-dicarboxyphenyl)hexafluoropropane dianhydride.

Madsen in U.S. Pat. No. 4,322,207 discloses dental cleaning slurry.

Beede et al in U.S. Pat. No. 4,324,591 discloses modifying agents for ion-leachable cement compositions.

Gibbs in U.S. Pat. No. 4,336,175 discloses polymide precursor solutions.

Schmitt et al in U.S. Pat. No. 4,372,836 disclose light curable acrylic dental composition with calcium fluoride pigment.

Smyth in U.S. Pat. No. 4,401,773 discloses highly reactive ion-leachable glass.

Denyer et al in U.S. Pat. No. 4,457,818 discloses dental compositions from urethane acrylate, diacrylate monomer, camphorquinone and dimethylaminoethyl methacrylate.

Ratcliffe et al in U.S. Pat. No. 4,459,193 discloses dental compositions containing camphorquinone and organic peroxide as catalyst.

Denton, Jr. et al in U.S. Pat. No. 4,492,777 discloses heat treated barium or strontium glass.

Bowen in U.S. Pat. No. 4,514,527 discloses method for obtaining strong adhesive bonding of composites to dentin enamel and other substrates.

Bowen in U.S. Pat. No. 4,521,550 discloses method for obtaining strong adhesive bonding of composites to dentin, enamel and other substrates.

Martin in U.S. Pat. No. 4,525,256 discloses photopolymerizable composition including catalyst comprising diketone plus 4-(N,N-Dimethylamino)benzoic acid or ester thereof.

Bowen in U.S. Pat. No. 4,588,756 discloses multi-step method for obtaining strong adhesive bonding of composites to dentin, enamel and other substrates.

Ratcliffe et al in U.S. Pat. No. 4,602,076 discloses photopolymerizable compositions.

Peters in U.S. Pat. No. 4,612,361 discloses poly(etherimides) and compositions containing the same.

Blackwell et al in U.S. Pat. No. 4,657,941 discloses biologically compatible adhesive containing a phosphorus adhesion promoter and a sulfinic accelerator.

Bowen in U.S. Pat. No. 4,659,751 discloses simplified method for obtained strong adhesive bonding of composites to dentin, enamel and other substrates.

Gallagher et al in U.S. Pat. No. 4,680,373 discloses process for the production of a random copolymer containing repeating polyimide units and repeating polyetherimide units.

Aasen et al in U.S. Pat. No. 4,719,149 discloses method for priming hard tissue.

Berdahl et al in U.S. Pat. No. 4,794,157 discloses polyetherimide copolymers, and method for making.

Engelbrecht et al in U.S. Pat. No. 4,806,381 discloses polymerizable compounds containing acid and acid derivatives, mixtures containing the same, and use thereof.

Blackwell et al in U.S. Pat. No. 4,816,495 discloses biologically compatible adhesive visible light curable compositions.

Calla et al in U.S. Pat. No. 4,864,015 discloses method for making thianthrene dianhydride and polyimides obtained therefrom.

Engelbrecht in U.S. Pat. No. 4,872,936 teaches dental cement mixtures containing polymerizable unsaturated monomers and/or oligomers and/or prepolymers containing acid groups and/or their reactive acid-derivative groups.

Aasen et al in U.S. Pat. No. 4,880,660 discloses method for priming hard tissue.

Kawaguchi et al in U.S. Pat. No. 4,918,136 discloses adhesive composition.

Ibsen et al in U.S. Pat. No. 4,964,911 discloses adhesive bonding of acrylic resins, especially in dentistry.

Huang et al in U.S. Pat. No. 4,966,934 discloses biological compatible adhesive containing a phosphorous adhesion promoter and accelerator.

Hirasawa et al in U.S. Pat. No. 4,985,198 discloses tooth-adhesive compounds.

Okada et al in U.S. Pat. No. 5,055,497 discloses curable resinous composition.

Akahane et al in U.S. Pat. No. 5,063,257 discloses dental glass ionomer cement compositions.

Wilson et al in U.S. Pat. No. 5,079,277 discloses polyvinylphosphonic acid and metal oxide or cermet or glass ionomer cement.

Mitra in U.S. Pat. No. 5,130,347 discloses photocurable ionomer cement systems.

Mitra et al in U.S. Pat. No. 5,154,762 discloses universal water-based medical and dental cement.

Ohno et al in U.S. Pat. No. 5,171,763 discloses curable composition.

Rambosek in Canadian Patent 873,935 discloses lithium aluminum silicate, polymer dental filling compositions.

Rossi in Canadian Patent 934,085 discloses dental restorative material of improved polishability.

Spoor in Canadian Patent 968,741 discloses production of coatings by curing with ionizing radiation.

Knight in Canadian Patent 969,299 discloses resins prepared from vinyl-ended polyurethane prepolymers.

Waller in Canadian Patent 983,190 discloses photopolymerizable acrylic dental products.

Lee et al in Canadian Patent 1,018,294 discloses dental filling package.

O'Sullivan in Canadian Patent 1,020,687 discloses urethaneacrylate dental filling composition.

Rockett et al in Canadian Patent 1,028,441 discloses three package dental restoration system.

Lorenz in Canadian Patent 1,117,242 discloses coating composition comprising N-vinyl-2-Pyrrolidone and an oligomer.

Osborn in Canadian Patent 1,131,388 discloses radiation curable urethane compositions.

Davies et al in Canadian Patent 1,136,796 discloses potopolymerizable compositions.

Skudelny et al in Canadian Patent 1,154,895 discloses flowable mixture and use of synthetic calcium silicate.

Schaefer in Canadian Patent 1,159,984 discloses dental material having a plastics material base.

Munk in Canadian Patent 1,164,124 discloses pourable solid mixture.

Chevreux et al in Canadian Patent 1,176,787 discloses photosetting adhesive composition.

Gruber et al in Canadian Patent 1,179,094 discloses radiation curable coating composition comprising an oligomer and a copolymerizable ultra-violet absorber.

Morgan in Canadian Patent 1,194,637 discloses UV and thermally curable, thermoplastic-containing compositions.

Ratcliffe et al in Canadian Patent 1,198,847 discloses dental Compositions.

Szycher et al in Canadian Patent 1,200,647 discloses actinic radiation cured polyurethane acrylic copolymer.

Temin et al in Canadian Patent 1,213,699 discloses dental restorative composition.

Moran in Canadian Patent 1,216,982 discloses cure to elastomers composition.

Ibsen et al in Canadian Patent 1,243,796 discloses dental composite and porcelain repair.

Ibsen in Canadian Patent 1,244,177 discloses methacrylate functional resin dental composite and porcelain repair compositions.

Ying in Canadian Patent 1,259,149 discloses dental restorative composition containing monofunctional monomer.

Randklev in Canadian Patent 1,261,992 discloses orthodontic bracket adhesive compositions.

Waknine in Canadian Patent 1,262,791 discloses a two component (Paste-Paste) self curing dental restorative.

Dougherty et al in Canadian Patent 1,262,981 discloses methods for posterior dental restoration employing light curable packable compositions.

Waknine in Canadian Patent 1,269,790 discloses dental restorative material.

Heid et al in Canadian Patent Application 2,009,471 discloses Hybrid plastic filling material.

Ibsen et al in Canadian Patent Application 2,011,438 discloses light-curable ionomer dental cement.

Rheinberger et al in Canadian Patent Application 2,038,695 discloses polymerizable dental materials.

Rheinberger et al in Canadian Patent Application 2,051,333 discloses polymerizable dental material.

Billington in European Patent Application 0 241 277 discloses glasses and poly(carboxylic acid) cement compositions containing them.

Billington in European Patent Application 0 244 959 discloses glass/poly(carboxylic acid) cement compositions.

Montgomery in European Patent Application 0 325 038 discloses surface priming composition for proteinaceous substrates, method of making and using same.

Kawaguchi et al in European Patent Application 0 335 645 discloses adhesive composition.

Griffin et al in European Patent Application 0 470 446 A1 discloses High glass transition temperature mixed polyimides and composites formed therefrom.

Masuhara in U.K. Patent Application 2 000 789 A discloses curable composition.

Hirasawa in U.K. Patent Application 2 156 347 a discloses (Meth) acrylic acid ester compounds boundable to tooth substrates.

Akahane et al U.K. Patent Application 2 202 221 discloses glass powders for dental glass ionomer cements.

U.S. Pat. No. 4,588,756 relates to aromatic based compositions employed in dentistry as a component in a dental adhesive system requiring multiple pretreatment steps including application of an acid.

Engelbrecht in U.S. Pat. No. 4,872,936 broadly teaches dental cement mixtures containing polymerizable unsaturated monomers and/or oligomers and/or prepolymers containing acid groups and/or their reactive acid-derivative groups.

Mitra in U.S. Pat. No. 5,130,347 discloses a photocurable ionomer cement having a photocurable amid monomer.

Mitra in U.S. Pat. No. 5,154,762 discloses water soluble reducing and oxidizing agents.

It is an object of the invention to provide a cement composition which reduces the steps and time required to adhere metal or ceramic to tooth structure.

It is an object of the invention is to provide new dental compositions useful as filling materials, cavity liners and bases, cements, and pit and fissure sealants.

It is an object to provide an adhesive cement composition for adhesion between tooth structure and/or bone and polymeric composites.

It is an object is to provide dental restorative/cement compositions that are relatively inexpensive and easy to manufacture.

It is an object of the invention to provide dental cements which are adhesive to tooth structure, and ceramics and metals.

It is an object of the invention to provide dental cement compositions useful as luting cements, pit and fissure sealants, filling and other restorative materials which are adhesive to tooth structure.

It is an object of the invention to provide compositions comprised of polymerizable partial esters of aromatic dianhydrides, and a source of cations capable of reacting with residual acid groups thereupon to further harden and/or crosslink the polymerized acid functional aromatic esters.

"Work time" as used herein means the time between mixing the components of a polymerizable composition and the time at which the composition is very viscous but pliable and not yet firm.

"Set time" as used herein means the time between mixing the components of a polymerizable composition and the time at which the composition becomes firm, stiff and nonpliable.

As used herein "The MAX Lite" means THE MAX ™, a resin curing unit for light-polymerizable dental materials sold by Dentsply International Inc. through its L.D. Caulk Division.

Throughout this disclosure unless otherwise specified amounts of each component of a composition are in percent by weight.

DETAILED DESCRIPTION OF THE INVENTION

Compositions of the invention provide superior adhesion to dentin, enamel and bone. In a preferred embodiment cement compositions of this invention are used without a separate step of etching the surfaces to be joined. The adhesive dental materials provided by this invention include restorative materials especially cavity bases and liners, luting cements, pit and fissure sealants and filling materials.

The dental materials of the invention include novel polymerizable partial esters of aromatic dianhydrides and a source of cations capable of reacting with residual acid groups to further harden and/or crosslink the resulting polymerized acid functional aromatic ester polymers.

Dental compositions of the invention include polymerizable unsaturated substituted aromatic compounds containing at least one acid moiety. These aromatic compounds are within the scope of the general formula (I):

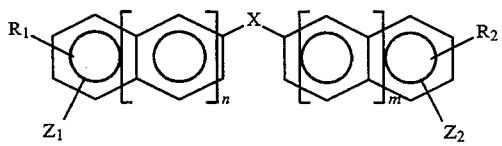

wherein
X, is O, S,

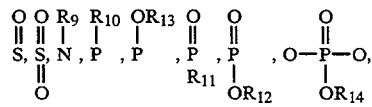

or 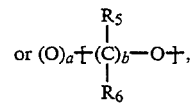

wherein $R_1$ and $R_2$ each independently is a polymerizable unsaturated moiety having from 2 to 13 carbon atoms, $R_3$, $R_4$, $R_5$, and $R_6$ each independently is hydrogen, halogen, alkyl having from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms.

$Z_1$ and $Z_2$ each independently is a moiety including an acid group or a reactive acid derivative, a, m and n each independently is 0 or 1, b and p each independently is an integer from 1 to 10.

In accordance with a preferred embodiment of the invention $R_1$ and $R_2$ each independently is:

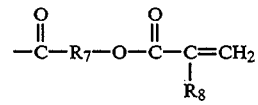

wherein $R_7$ a divalent carbon containing radical and $R_8$ is hydrogen, halogen or alkyl having from 1 to 10 carbon atoms.

In a preferred embodiment of the invention compounds are provided within the scope of general formula I wherein n and m are zero, X is oxygen, sulfonyl or ditrifluoromethyl; $Z_1$ and $Z_2$ are —COO(M) wherein M is hydrogen or an alkali metal, alkaline-earth metal, amine or amine salt; and $R_1$ and $R_2$ are

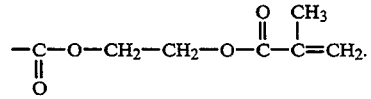

Most preferably compounds within the scope of general formula I are those wherein X is oxygen, and M is hydrogen, Li, Na or K. Appropriate polymerizable unsaturated groups $R_1$ and $R_2$ independently are alkenyl, alkenoxy, cycloalkenyl, arylalkenyl, and alkenaryl moieties; with vinyl, and styryl moieties being preferred, and acryl and methacryl moieties that constitute the polymerizable groups of many monomers in dental materials being especially preferred.

Exemplary $R_1$ and $R_2$(meth)acrylate moieties include:

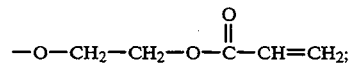

-continued

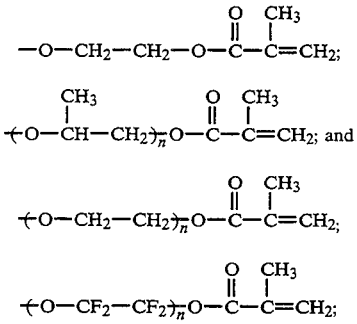

where n preferably is an integer from 1 to 10. Preferably $R_1$ and $R_2$ are (meth)acryloyloxyethyl moieties.

Preferred compounds within the scope of formula I include diesters which are the adducts of 4,4'-oxydiphthalic anhydride, 2,2-bis (3,4-dicarboxylphenyl)hexafluoropropane anhydride, 4,4'-sulfonyldiphthalic anhydride, respectively with 2-hydroxyethyl methacrylate. In a preferred embodiment at least two aromatic rings of a compound with the scope of formula I are joined through at least one saturated carbon, oxygen or sulfonyl.

Aromatic dianhydrides preferred for making compounds within the scope of general formula I react to form partial esters and carboxylic acid functionality. Dianhydrides having at least two aromatic rings are more preferred. Most preferably at least two aromatic rings are joined as shown in formula I to provide disruption of conjugation between the aromatic rings. It has been found that such compositions are less sensitive to light induced changes in color, and are therefore preferred when esthetic considerations are of importance. Most preferred examples are 4,4'-oxydiphthalic anhydride and 2,2-bis(3,4-dicarboxyphenyl)hexafluoropropane dianhydride.

Dental cement compositions in accordance with a preferred embodiment of the invention include an acid functional polymerizable organic ester within the scope of general formula I, water, cation elutable glass filler, and a polymerization catalyst system. Optionally, additional polymerizable monomers and/or prepolymers are included.

A composition in accordance with a preferred embodiment of the invention provides polymerizable monomer having at least one acid radical or reactive acid derivative, and a source of cations reactive with the acid moiety, and a catalyst system. Preferably the catalyst system promotes free radical polymerization and preferably includes visible light curing and/or a redox catalyst system. Preferably the composition includes liquid diluents, and/or filler adjuvants. Diluent preferably co-polymerizes with the polymerizable monomer within the scope of general formula I. Alternatively the diluent is nonreactive with the polymerizable monomer. Water for example is a nonreactive diluent. Suitable polymerizable co-monomers are disclosed in U.S. Pat. No. 4,657,94 1 particularly at column 3 line 5 through column 5 line 59 and U.S. Pat. No. 4,514,342 both of which are incorporated herein by reference. The filler adjuvants are preferably reactive, for example by providing a source of cations which are reactive with the acid moiety of the polymerizable monomer. Nonreactive filler is preferably included in compositions in accordance with a preferred embodiment of the invention.

Optionally, fillers have surface treatments to improve compatibility and strength of the resulting composition. Exemplary fillers include silica, silicates, alumina, aluminates, calcium fluoride, strontium fluoride, glasses including fluorine glasses, ceramics and minerals including mica, zeolites, ceramics, calcium apatites and organic polymers and those disclosed in U.S. Pat. Nos. 4,758,612 and 5,079,277.

In accordance with a preferred embodiment a liquid and a powder are mixed to form a dental cement composition. The liquid includes polymerizable monomer within the scope of formula I, and the powder includes a source of cations reactive with the polymerizable monomer. The liquid preferably includes diluent. The powder composition preferably includes a free radical polymerization catalyst system, and a glass powder which provides a source of cations and filler adjuvants.

A preferred composition of the invention includes a monomer compound within the scope of general formula I, at least one finely divided reactive filler which provides a source of cations reactive with the acids or acid derivative of the monomer compound and curing agent. A dental luting cement composition in accordance with the invention includes a compound of general formula I, catalysts, initiators, accelerators, filler, adjuvants, source of cations, water, and diluent. Dental cements and dental filling compositions in accordance with a preferred embodiment of the invention include monomer compounds within the scope of general formula I.

The compounds within the scope of general formula I have at least two different functional substituent groups, one of which is capable of addition polymerization and the other of which is carboxyl or-other acid or reactive acid derivative. Most preferably these compounds include at least one polymerizable group and one or more acid or reactive acid derivative groups. Preferred compounds within the scope of general formula I are derived from the reaction of 4,4'-oxydiphthalic anhydride or 2,2-bis(3,4-dicarboxylphenyl)hexafluorpropane dianhydrides with a hydroxyl or polyhydric compound to form esters and partial esters thereof.

The new compounds of the invention are capable of being polymerized to form linear or crosslinked polymers which contain multiple acid groups or reactive acid derivative groups that may be further reacted with cations, especially those of valence 2 or greater to form poly-salts relatively insoluble in water. Because the compounds are monomers of relatively low molecular weight with a high density of both ethylenic unsaturation and carboxylic reactive acid derivative sites, excellent curing with superior integrity occurs. The cations may be supplied by ingredients or components of the given formulation or they may be supplied from a solution of cations supplied from a second component of the formulation, or they may be supplied from the substrate against which the formulation is polymerized especially the tooth in the preferred dental compositions where this provides strong bond in the preferred applications. In such a case the carboxyl ions, other acid ions or reactive acid derivative ions may be chelated with surface cations of the substrate to provide an adhesive bond. In a preferred dental composition not only is this substrate bonding available but bonding with an ion contributing inorganic filler aids in binding the entirety-together. It will be understood that the term reactive acid derivative ions as used here includes the water compatible salts, and others of cations, especially the monovalent species of cations, for example the lithium, sodium, ammonium and potassium salts, which are displaced by cations of greater valency by metathesis. However, the carboxyl group itself is most preferred over other acid moieties or the reactive acid derivative ions. Especially appropriate acid moieties are all those that can react with oxidic, mineral, ceramic, vitreous, or metallic fillers.

Examples of these other acid moieties include:

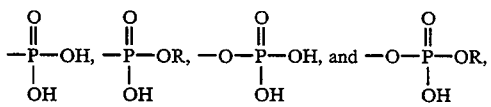

of phosphorus acids wherein R is alkyl, aryl, or vinyl; the moieties $-SO_2H$, $SO_3H$, or $-O-SO_3H$ of sulfuric acids; the moieties:

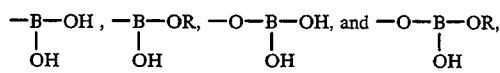

of boron acids wherein R is alkyl, aryl, or vinyl and cationic acid moieties including $-NR_2H+$ wherein R is H or alkyl. The reactive acid derivatives can be substituted with acid halides, with acid anhydrides, and with acid amides, nitriles, and esters that readily-hydrolyze into acid, such as can enter into ion-exchange, neutralization, salt formation, or chelation reactions with the reactive filler. Preferred acid or reactive acid derivatives are carboxylate, phosphate, phosphonate, sulfonate, or borate acid moieties and/or of their reactive derivatives.

The compositions of the invention are formulated as one, two or more components, visible light curable, self cure, and/or dual cure product or combinations of these. The composition of a preferred embodiment of the invention includes polymerizable carboxylic acid monomer, an optional filler and/or diluent, a cationic elutable glass-or other source of polyvalent cations, and a polymerization catalyst system. The polymerizable carboxylic acid monomers are chosen to provide a suitable balance of hydrophobic and hydrophilic moieties in order to provide a balanced set of properties including adhesion to metal, ceramics and tooth. They are essentially non-volatile and provide cement compositions that are prompt setting and not critically affected by moisture during hardening within the oral cavity; strength at least as great as zinc phosphate cement in a particular embodiment intended for permanent cementation; and provide the ability to be used on hydrated surfaces such as found on and in teeth; and in a preferred embodiment do not require the separate steps of acid etching and adhesive priming to achieve adhesion to tooth structure.

For a better understanding of the characteristics and method of producing the preferred ethylenically unsaturated carboxylic acid monomer compounds of the present invention the preparation of a preferred series of the compounds of the invention is carried out as follows:

In the presence of acid, base or other suitable catalyst one mole 4,4' oxydiphthalic anhydride is reacted with two moles of a compound of the general formula R—OH, wherein R is a polymerizable unsaturated moiety having from 2-13 carbon atoms. This yields a liquid product which is believed to be a mixture of isomer monomers of general formulas II-IV:

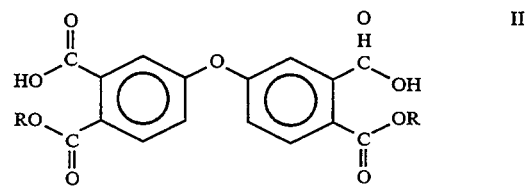

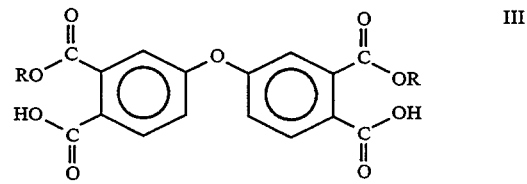

and

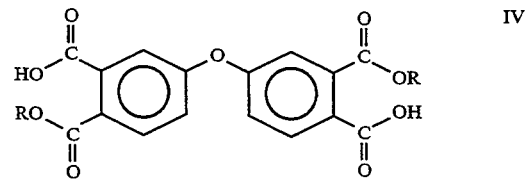

As discussed in detail in Example 3 below by reacting one mole of oxydiphthalic anhydride with two moles of methacryloyloxyethyl alcohol also known as 2-hydroxyethyl methacrylate (HEMA) in the presence of $H_2SO_4$ a liquid product is formed which is believed to be a mixture of isomer monomers V-VII:

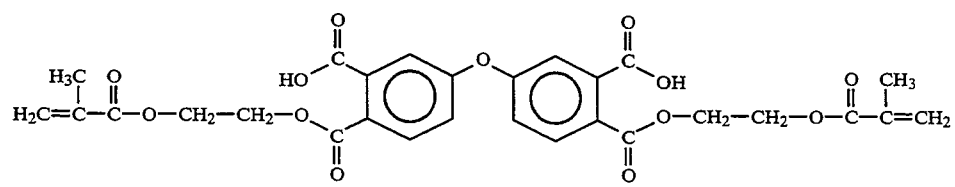

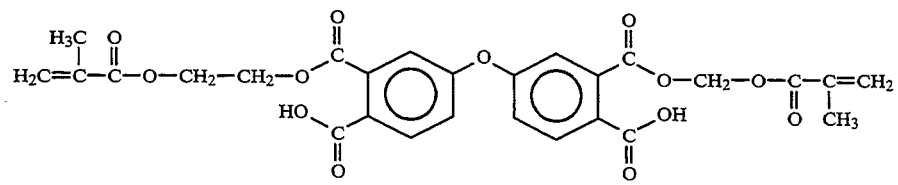

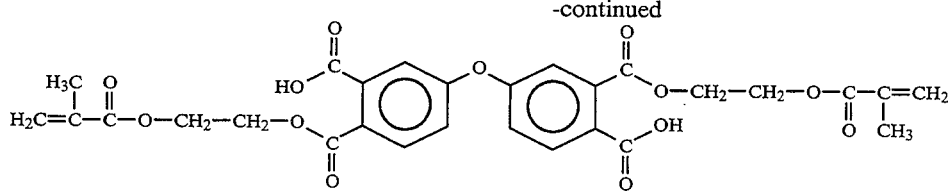

Monomer compounds within the scope of general formula I are reactive esters which have at least one unreacted carboxylic acid group and one polymerizable group in the monomer. The number of reacted or unreacted carboxylic acid groups in the monomer is controlled by varying the reaction conditions and molar ratio of reactants. The monomer compounds of the invention polymerize by addition polymerization through the ethylenically unsaturated group. Curing agents, catalysts, initiators and/or accelerators, are used to expedite and control the polymerization. A peroxide initiator, for example benzoyl peroxide, and/or heat are useful to initiate the reaction. Accelerators enhance the reaction so that it may proceed more expeditiously at room temperature. Accelerators preferably include reducing agents such as amines or sulfinates, and/or transition metal ions. Ultraviolet and/or visible light are used with initiators and accelerators to initiate and accelerate the polymerization. Visible light curing is preferred for curing the compositions of the invention in the mouth. For preformed objects, or those cured outside the body, other forms of radiation, for example ultraviolet ionizing radiation is preferred for curing the compositions of the invention.

In accordance with the method of the invention invivo polymerization does not harm the patient within whom polymerization of monomer compound within the scope of general formula I occurs. The polymerization catalyst system, for example a peroxide and an amine, is preferably formulated as two parts. Polymerization is delayed until both parts are combined and react to polymerize the monomer. Alternatively a single part composition is induced to polymerize by the application of heat or light. To initiate by irradiation with ultraviolet or visible light the initiator, for example a benzophenone or camphorquinone is preferably combined within a single, premixed, ready to use shelf-stable composition. A preferred embodiment of the composition of the invention includes a polymerization catalyst system having a light sensitive polymerization initiator such as camphorquinone, a reducing agent such as ethyl 4-dimethylaminobenzoate (EDAB) and an oxidizing agent such as benzoyl peroxide. Redox polymerization systems known to the art are preferably used to polymerize the composition of the invention. Preferred redox polymerization catalyst systems for use in accordance with the invention include, a peroxide and tributyl boron and/or a transition metal salt. Redox polymerization catalysts and catalyst systems are those disclosed in U.S. Pat. No. 4,657,941 at column 7 line 10 through column 8 line 27 incorporated herein by reference. A particular polymerization method and system may be preferred depending on the application requirements of the material. Whatever the mode of polymerization, or "cure" of the composition including the monomers, an important characteristic of the polymers which form are that they are capable of further reaction with di- or polyvalent cations to crosslink the product. The compounds and compositions of the invention are adapted to form or include resin which exhibit adhesion between the resin and a cation containing surface, metal, metal oxide, tooth, and/or bone against which they are polymerized.

Fillers which are especially suited for use in compositions of the invention are inorganic glasses such as are used in glass ionomer cements. Exemplary of such fillers are those of U.S. Pat. No. 4,814,362 which is incorporated herein by reference in its entirety. Preferred fillers are glasses formed from or including, barium, calcium, strontium, lanthanum, tantalum, and/or tungsten silicates and aluminates and/or aluminosilicates, silica, including submicron silica, quartz, and/or ceramics for example, calcium hydroxy apatite. In a preferred embodiment of the invention reactive cations, especially those of calcium, strontium and aluminum, and anions especially fluoride ions; are eluted from the fillers. The fillers used in the invention preferably are reduced in particle size and are preferably silanated before they are incorporated into such compositions. Preferred levels of filler are from about 20% to about 85% based on the total weight of the cement composition, with from about 40% to about 85% being more preferable and about 50–80% being most preferred. If a more finely particulated filler is used, amounts of filler may be decreased due to the relative increase in surface area which attends the smaller sizes of particles. Preferred particle size distributions are from 0.02 to 50 microns, more preferably 0.1 to 10 microns, and most preferably 1 to 6 microns.

In a preferred embodiment sources of cations, for example salts of di- and polyvalent cations such as $SrF_2$ are preferably used to crosslink the products of the invention. In another preferred embodiment compositions of the invention include solvents, plasticizers, pigments, anti-microbials and oxidation inhibitors such as butylated hydroxytoluene. In addition to compounds within the scope of general formula I compositions in accordance with the invention preferably include polymerizable unsaturated diluent monomers and/or oligomers and/or prepolymers that do not contain any acid groups and/or salts thereof and/or reactive readily hydrolyzing acid-derivative groups thereof. One such preferred monomer is hydroxyalkyl methacrylates. Compositions of the invention may also preferably include compounds having acid groups and/or their salts and/or their reactive readily hydrolyzing derivative groups but do not contain any groups that are unsaturated and polymerizable, such as multi-basic acids or their reactive, readily hydrolyzing derivatives. Especially preferred multibasic acids are hydroxy acids such as tartaric or citric acid, but also preferred are polyacids such as polycarboxylic, polyphosphoric, polyphosphonic, or polysulfonic acids.

Compounds that have chelating groups but do not contain carboxylic acid groups or readily hydrolyzing acid-derivative groups are preferably included in composition in accordance with the invention, for example vanillates, syringates, and salicylates. Non-reactive diluents are also desirable to more completely and quickly wet substrates. Suitable diluents are ethanol, acetone, water, and less viscous reactive monomers.

Mixing the compositions of the present invention may be achieved using standard compounding techniques. For example, liquids, photoinitiator(s), and accelerator(s) are blended first, and fillers are added incrementally thereafter. When blending light sensitive compositions, however, a photosafe room illumination, i.e., one that does not contain substantial amounts of wavelengths of electromagnetic radiation that would activate the photoinitiating system is used to avoid initiating polymerization of the composition prematurely.

CEMENTS

The compounds of the present invention also have medical applications such as in self adhesive bone cements. However, they are most preferred to use in dental treatment by application to a tooth or a number of teeth in vivo, in the mouth of a live patient by a dentist or dental practitioner.

The application of the compositions of the invention is preferably as a dental cement applied to tooth. The dental cement compositions of the invention preferably include a compound within the scope of general formula I, a source of cations, and other ingredients, such as curing catalysts, initiators, accelerators, diluents and/or adjuvants. The composition is applied as a cement using conventional techniques and preferably cured with application of visible light in a conventional manner. Cements in accordance with the invention are self adhesive to dentin and enamel. These cements are used in bonding dentin to structures, for example, to bond a ceramic inlay to a prepared cavity of a tooth. Inlays preferably are polymers, or ceramics which are cast or built-up from porcelain frits and fired. Alternatively, inlays are machined from metal such as titanium or gold or preformed polymeric composite or homogeneous monolithic polymer compositions, for example by CAD-CAM procedures. In accordance with a preferred embodiment of the invention metal or ceramic superstructures for crowns, and bridges and/or orthodontic appliances are bonded to teeth using cement compositions of the invention. Such cement compositions join metal or ceramic to tooth by application of the cement composition by bringing them into contact until the cement hardens.

A preferred composition of the invention includes a two-part system. One part includes a curing agent. The two parts are spatuled to form a cement prior to placement on tooth. The placement is by standard technique(s). Preferably the cement includes a visible light and/or a self-curing redox polymerization initiator system. In a preferred embodiment of the invention luting cement compositions have low viscosity and film thicknesses less than about 25 $\mu$m to bond close fitting appliances to prepared teeth. In one embodiment luting cement compositions of the present invention may be prepared of such high viscosity and consistency that they form adhesive "glue" lines of thicknesses up to several hundred microns to lute less close fitting restorations, for example inlays prepared using present state-of-the-art CAD-CAM devices. Compositions of the invention are mechanically strong, abrasion resistant, and are esthetically suitable and serve as the sole structural element to retain inlay, crowns and bridges or other appliances to tooth structure.

FILLING COMPOSITIONS

A preferred dental treatment in accordance with the invention is the application of dental filling compositions which include a curing agent and at least one compound within the scope of general formula I. Preferably the dental filling composition includes finely divided reactive filler that can react ionically with the acids or acid derivatives of the monomer. Preferably the composition is applied to a tooth as a filling material using conventional techniques as a one-component material and is cured with application of visible light in conventional manner.

PIT AND FISSURE SEALANTS

In a preferred embodiment of the invention a one or two component pit and fissure sealant which includes at least one compound within the scope of general formula I is applied to anatomic defects and/or the exterior of teeth. The sealant limits the ability of caries-forming bacteria to colonize the pits, fissures and other surfaces of the teeth. Pit and fissure sealant compositions in accordance with the invention are an especially Valuable means of reducing caries by filling and eliminating enamel defects. The pit and fissure sealants of the invention are preferably applied without prior acid etching or the use of rubber dam to teeth. In one embodiment fluoride eluting compounds and glasses are preferably included in compositions of the invention. Fluoride is eluted to reduce the incidence of caries in tooth substance adjacent the compositions of the invention.

In accordance with the method of the invention cement and restorative compositions include at least one polymerizable acid reactive ethylenically unsaturated compound within the scope of general formula I. Such compositions are applied to tooth without prior etching of the tooth.

Method for Measurement of Compressive Strength Using International Standard Organization(ISO) 9917:1991(E) at Pages 5–7 Dental Water-based Cements For each material to be tested, cylinders 4 mm diameter and 6 mm long were prepared by filling the mixed material into teflon molds and light curing from each end for 40 seconds using The MAX Lite. The cylinders were removed from the molds and stored in water at 37° C. for 24 hours prior to testing. The force needed to load the specimens to breaking point was measured using a universal testing machine operating at a crosshead speed of 1 mm/min.

Method of Transverse Flexural Strength Using International Standard Organization(ISO)4049: 1988(E) at Pages 6–8 Resin-based Filling Materials The uncured material was filled into a split Teflon ® mold with internal dimensions 25 mm×2 mm×2 mm. The exposed faces were then covered with polyester foil and clamped between transparent plastic blocks. The material was light cured for a total of 120 seconds by moving a dental curing light evenly backwards and forwards along the mold with the wand of the light in contact with the plastic blocks. After curing, the hardened specimens were stored in water at 37° C. for 24 hours. Before being tested, any remaining flash along the edges of the specimens was carefully removed and the exact dimensions of each specimen measured. The specimens were then tested in three point bending mode using a universal testing machine set to a crosshead speed of 1 mm/min, with the sample resting on supports 20 mm apart and being loaded at the mid point. The transverse bending strength was calculated from the standard formula in Megapascals (MPa).

Method for Measurement of Diametral Tensile Strength

Modified procedures of ADA Specification No. 9 and No. 27 were utilized for all materials tested. Split teflon molds with internal dimensions of 3 mm±0.1 mm high and 6 mm±0.1 mm diameter were used. Mylar film was placed at the bottom of the mold. After the mixed material was conveyed into the mold in excess, a second piece of mylar film was placed on top of the mold and pressed with a metal plate to squeeze out excess material. The plate was then removed with the mylar still in place on top of the material and each side was cured for one minute using The MAX Lite. After being stored in 37° C. water for 24 hours, specimens were tested on an Instron device for measurement of diametral tensile strength rising a 10 mm/minute crosshead speed.

Measurement of Adhesion to Dentin: Bond Strength to Dentin

Extracted human teeth used for the shear bond strength test was treated in 1% sodium hypochlorite for 18 to 24 hours and stored in distilled water in a refrigerator at about 4° C. until needed. The teeth were washed with water, mechanically sanded with 120/320/600 grit carborundum paper until a flat dentin surface was exposed.

The teeth were then individually prepared as follows. Each tooth was blown dry with compressed dry air to ensure the dentin surface was free from noticeable moisture. A small plastic straw with 3.7 mm inner diameter and 2 to 3 mm in length was filled with mixed material and seated on the dentin so as to form a post without pressure. The upper open end of the straw was covered with a thin film and cured with The MAX Lite for 40 seconds. The specimens were then stored in distilled water at 37° C. for more than 24 hours. The teeth were then vertically mounted in a one inch phenolic ring using self curing polymethyl methacrylate resin to provide a base for testing with the post at right angles thereto. The mounted specimens were loaded in shear in an Instron device for measurement of adhesion of the post to dentin at 5 mm/minute crosshead speed. The load was applied parallel to the prepared tooth surface and at right angles to the post until fracture occurred. The shear bond strength was calculated.

Method of Measuring Fluoride Release

Four 1×20 mm (diameter) discs of each material were made and conditioned to a constant weight. The initial average weight in grams was recorded. Duplicate setups were used. Each setup consisted of a 500 ml flask which contained 300 ml deionized water, Soxhlet containing two specimens in the thimble, and a water condenser. The specimens were extracted for 24 hours by refluxing water. The water extract was cooled to room temperature and measured for fluoride content. Then, the Soxhlet extraction were repeated with fresh deionized water for six more times.

Using an ion selective electrode, the fluoride concentration in parts per million(ppm) was determined for each extract. The average ppm of the duplicates were recorded.

Having generally described the invention, a more complete understanding can be obtained with reference to certain specific examples, which are included for purposes of illustration only. It should be understood that the invention is not limited to the specific details of the Examples.

EXAMPLE 1

6FDMA is the reaction product of 1 mole of hexafluoroisopropylidine-2,2 bis(phthalic acid anhydride) and 2 moles of 2-hydroxyethyl methacrylate, identified hereafter as 13.3 grams (0.03 moles) hexafluoroisopropylidine-2,2bis (phthalic acid anhydride) and 12.6 grams (0.097 moles) of HEMA and 0.6 grams of butylated hydroxytoluene are heated in a 100 ml round bottom flask equipped with a thermometer and a water cooled condenser with a drying tube. The mixture is stirred while heating slowly to 100° C. Thereafter the temperature is maintained at 110° C. for one hour, then 16 hours overnight at 50° C., then a further 3.5 hours at 110° C. The solution is cooled to room temperature. The solution contains 70% by weight of 6FDMA and 30% by weight of HEMA and has IR absorptions at: 2500–3500 cm$^{-1}$, broad; 1715 cm$^{-1}$ broad; 1630 cm$^{-1}$; 1130–1450 cm$^{-1}$ broad; 1170 cm$^{-1}$; 950 cm$^{-1}$; and 800 cm$^{-1}$ multiplet.

EXAMPLE 2

Synthesis of BTDMA

BTDMA is the reaction product of 1 mole of 3,3',4,4'-benzophenone tetracarboxylic acid dianhydride and 2 moles 2-hydroxyethyl methacrylate. When prepared in an excess of 2-hydroxyethyl methacrylate the HEMA serves as a solvent for the esterification reaction.

50 grams (0.155 moles) 3,3',4,4'-benzophenone tetracarboxylic acid dianhydride (Aldrich Chem) is reacted with 82.7 grams HEMA (0.635 moles) (Aldrich Chemical) at 120° C. for 1 hour to provide a clear thick liquid containing BTDMA in an excess HEMA, having IR absorptions at 3000 to 3550 cm, $^{-1}$, very broad; 2950 cm$^{-1}$ broad; 1720 cm$^{-1}$, broad; 1630 cm$^{-1}$; 1370–1450 cm$^{-1}$ multiplets; 1100–1340 cm$^{-1}$ very broad; 1160 cm$^{-1}$; 940 cm$^{-1}$; 810 cm$^{-1}$; and 650 cm$^{-1}$. This solution contains 70% by weight of BTDMA and 30% of HEMA.

EXAMPLE 3

Synthesis of OEMA

OEMA is the reaction product of 1 mole 4,4' oxydiphthalic anhydride (chemical name: 5,5'-oxybis-1,3-isobenzo furandione) and 2 moles of HEMA.

35.6 grams (0.115 moles) of 4,4'-oxydiphthalic anhydride and 58.0 grams (0.045 moles) of HEMA are reacted at 110° C. for 4 hours to provide a clear oily solution of OEMA in an excess of HEMA, having a viscosity of 5250 cps, and IR absorptions at 2700–3550 cm$^{-1}$ very broad; 1715 cm$^{-1}$ broad; 1630 cm$^{-1}$, 1590cm$^{-1}$; 1570 cm$^{-1}$; 1450 cm$^{-1}$; 1400 cm$^{-1}$; 1360 cm$^{-1}$; 1100–1330 cm$^{-1}$; 1165 cm$^{-1}$; 940 cm, $^{-1}$; 810 cm$^{-1}$, and 785 cm$^{-1}$. This solution contains 70% by weight OEMA and 30% by weight of HEMA.

EXAMPLE 4

Synthesis of OPMA

OPMA is the reaction product of 1 mole oxydiphthalic anhydride and 2 moles of HPMA.

18.0 grams (0.058 moles) of 4,4' oxydiphthalic anhydride (Occidental Petroleum) and 32.6 grams (0.226 moles) HPMA (Aldrich) are reacted at 110° C. while stirring for 3 hours at 110° C. to provide a clear oily solution of OPMA in an excess of HPMA having a viscosity after reaction of 3250 cps at 23° C. and the OPMA having IR absorptions at 3100–3550 cm$^{-1}$ very broad; 2900–3000 cm$^{-1}$; 1715 cm$^{-1}$; 1630 cm$^{-1}$; 1590 cm$^{-1}$; 1570 cm$^{-1}$; 1445 cm$^{-1}$; 1400 cm$^{-1}$; 1100–1330 cm$^{-1}$; 1060 cm$^{-1}$; 940 cm$^{-1}$; 810 cm$^{-1}$. This solution contains 70% by weight OPDMA and 30% by weight of HEMA.

EXAMPLE 5

Preparation of STDMA

STDMA is the reaction product of 1 mole of 4,4' sulfonyldiphthalic dianhydride (STDA) and 2 moles of HEMA. In this example STDMA is prepared in an excess of HEMA.

26.9 grams (0.207 moles) HEMA, 10.4 grams (0.029 moles) STDA and 0.044 grams BHT are placed in a 100 ml flask and heated to 90° C. The mixture is held for 1.5 hours at 90° C. to 95° C. and 1.33 hours at 115° C. to 120° C. Then 0.11 grams triphenyl phosphine, 10.2 grams (0.028 moles) STDA, and 4.3 grams (0.033 moles) HEMA are added to the mixture and held at 115° C. to 120° C. for an additional 1.5 hour to form a solution containing 68.6% by weight of STDMA and 31.4% by weight of HEMA having IR absorptions at 3500 cm$^{-1}$, very broad; 1715 cm$^{-1}$ 1635 cm $^{-1}$; 1300 cm$^{-1}$ broad, and 1150 cm$^{-1}$ broad. This solution contains 68.6% by weight of STDMA and 31.4% by weight of HEMA.

EXAMPLE 6

Preparation of OEMA in TEGMA

OEMA is the reaction product of 1 mole of oxydiphthalic dianhydride (ODPA) and 2 moles of HEMA.

In this example product is prepared in triethylene glycol dimethacrylate (TEGDMA) as a solvent.

19.6 grams (0.063 moles) of ODPA, 30 grams (0.23 moles) HEMA, 0.046 grams of monomethyl hydroquinone and 20 grams of TEGDMA as a solvent are placed in a 250 ml flask. The mixture is heated with stirring to 95° C. to 100° C., and 0.06 grams triphenyl phosphine as catalyst is added and held at 100° C. for an additional 25 minutes. Following this 15.5 grams (0.05 moles) of ODPA and 0.03 grams of triphenyl phosphine are added at 110° C. After stirring at 110° C. for 1.5 hours, 0.02 grams of triphenyl phosphine is added and held for one hour at 110° C. and then held at 50° C. for 7 days. At the end of that time all anhydride is consumed. The reaction forms a solution containing 76.5% by weight OEMA and 23.5% TEGMA. The OEMA which has IR absorptions at 2500 to 3550 cm$^{-1}$ very broad; 1700 cm$^{-1}$ broad; 1630 cm$^{-1}$, 1100–1450 cm$^{-1}$ very broad; 1050 cm$^{-1}$; 950 cm$^{-1}$; and 780–900 cm$^{-1}$. This solution contains 76.5% by weight of OEMA and 23.5% by weight of TEGMA.

Preparation of Powders in Examples 7–9 for Use in Examples 10–16

Strontium aluminofluorosilicate glass used to make powders in Examples 7–9 is a source of cations in the cement compositions of Examples 10–16, and is made by fusing aluminum oxide, silica, strontium fluoride, aluminum fluoride, aluminum phosphate, and cryolite according to procedures disclosed in U.S. Pat. No. 4,814,362 to form particles which are milled to a mean particle size of 5.5 microns. These particles have the following analysis with all elements except fluorine being calculated as the oxide of the element:

| Composition of aluminofluorosilicate glass particles | Parts by weight |
| --- | --- |
| $Al_2O_3$ | 24.6 |
| $SiO_2$ | 32.1 |
| $Na_2O$ | 2.9 |
| SrO | 28.7 |
| F | 12.3 |
| $P_2O_5$ | 4.8 |

EXAMPLE 7

Powder is prepared by placing 98.78 grams of strontium aluminofluorosilicate glass powder, 1.0 grams of benzoyl peroxide and 0.2 grams of ascorbyl palmitate and 0.02 grams of cupric acetylacetonate in a bottle and tumbling for an hour, and passing the tumbled mixture through a 325 mesh sieve to form a powder product.

EXAMPLE 8

Powder is prepared by placing 79.0 grams of strontium aluminofluorosilicate glass powder, 1.0 grams of benzoyl peroxide, 0.2 grams of ascorbyl palmitate 0.02 grams of cupric acetylacetonate and 19.6 grams of barium aluminum silicate glass powder (Corning Incorporated 7724 glass) having an average particle size of 1 micron in a bottle and tumbling for an hour, and then passing the tumbled mixture through a 325 mesh sieve to form a powder product.

EXAMPLE 9

Powder is prepared by placing 79.2 grams of strontium aluminofluorosilicate glass powder, 20.0 g barium aluminum silicate glass powder, and 0.8 grams of ethyl dimethylaminobenzoate in a bottle and tumbling for an hour, and passing the tumbled mixture through a 325 mesh sieve to form a powder product.

As discussed above the powders of Examples 7–9 are prepared by mixing the components of each composition as in the proportions given in parts by weight shown in Table 1.

TABLE 1

|  | Composition of the powder of Example 7 | Composition of the powder of Example 8 | Composition of the powder of Example 9 |
| --- | --- | --- | --- |
| Strontium aluminofluorosilicate glass | 98.78 | 79.0 | 79.2 |
| Benzoyl peroxide | 1.0 | 1.0 | — |
| ascorbyl palmitate | 0.2 | 0.2 | — |
| cupric acetylacetonate | 0.02 | 0.02 | — |
| barium alumina silicate | | 19.6 | 20.0 |
| ethyl dimethylamino benzoate | | | 0.8 |

EXAMPLE 10

Cement 95 grams of a solution of 70% by weight 6FDMA and 30% by weight HEMA prepared as described in Example 1 is stirred with 5.0 grams of water to form a liquid formulation. 1 gram of this liquid formulation is mixed with 2 grams of powder product prepared as described in Example 7. This mixture reacts with a work time of 3.0 minutes and a set time of 4.0 minutes to form a cement having a bond strength to dentin of 13.8 MPa, a bond strength to enamel of 9.7 MPa.

EXAMPLE 11

Cement 95 grams of thick liquid containing BTDMA in an excess of HEMA prepared as described in Example 2 is stirred with 5.0 grams of water to form a liquid formulation. 1 gram of this liquid formulation is mixed with 2 grams of powder product prepared as described in Example 7. This mixture reacts with a work time of 2.3 minutes and a set time of 3.5 minutes to form a cement having a bond strength to dentin of 7.6 MPa, a bond strength to enamel of 10.2 MPa, a diametral tensile strength of 28.6 MPa, and a compressive strength of 116 MPa.

EXAMPLE 12

Cement 90 grams of oily solution of OEMA in an excess of HEMA prepared as described in Example 3 is stirred with 10.0 grams of water to form a liquid formulation. 1 gram of this liquid formulation is mixed with 2 grams of powder product prepared as described in Example 7. This mixture reacts with a work time of 2.5 minutes and a set time of 3.5 minutes to form a cement having a bond strength to enamel of 9.4 MPa, a diametral tensile strength of 32.3 MPa, a compressive strength of 130 MPa, and a bond strength to amalgam of 17.9 MPa.

EXAMPLE 13

Cement 95 grams of oily solution containing OPMA in an excess of HPMA prepared as described in Example 4 is stirred with 5.0 grams of water to form a liquid formulation. 1 gram of this liquid formulation is mixed with 2 grams of powder product prepared as described in Example 7. This mixture reacts with a work time of 2.5 minutes and a set time of 3.5 minutes to form a cement having a bond strength to dentin of 6.3 MPa, a bond strength to enamel of 18.6 MPa, a diametral tensile strength of 27.0 MPa, a compressive strength of 120 MPa and a bond strength to amalgam of 20.2 MPa.

EXAMPLE 14

Cement 85.9 grams of STDMA prepared in an excess of HEMA as described in Example 5 is stirred with 8.0 grams of water and 6.1 grams of HEMA to form a liquid formulation. 1 gram of this liquid formulation is mixed with 2 grams of powder product prepared as described in Example 7. This mixture reacts with a work time of 2.5 minutes and a set time of 3.0 minutes to form a cement having a bond strength to dentin of 6.5 MPa, a diametral tensile strength of 26.7 MPa, and a compressive strength of 139 MPa.

EXAMPLE 15

Cement 91.8 grams of oily solution containing OEMA in an excess of HEMA prepared as described in Example 3 is stirred with 8.0 grams of water and 0.20 grams camphorquinone to form a liquid formulation. 1.0 gram of this liquid formulation is mixed with 1.8 grams of powder product prepared as described in Example 9. This mixture reacts (with a work time of 10 minutes and a set time of 120 minutes if allowed to self-cure), and is irradiated with visible light from The MAX Lite having a bond strength to dentin of 11.7 MPa, a diametral tensile strength of 37.2 MPa, and a compressive strength of 154 MPa.

EXAMPLE 15A

Self-curing, Two Component, Powder and Liquid Cement 0.92 grams of the liquid prepared as described in Example 3 and 0.08 grams of water are dissolved in one another to form a liquid. 1.0 grams of this liquid is added to 2.0 grams of the strontium aluminofluorosilicate containing powder of Example 7. The consistency of the mixture is suitable for use as a luting or crown and bridge or orthodontic cement or as a pit and fissure sealant. Polymerization is induced by the redox polymerization system of benzoyl peroxide, ascorbyl palmitate and copper acetyl acetonate. The liquid contains 8.0% water, and wets the tooth when the cement is applied. The powder and liquid compositions are as follows:

|  | PERCENT BY WEIGHT |
|---|---|
| POWDER | |
| Strontium fluoroaluminosilicate cement (Glass of example 7) | 98.83 |
| Benzoyl peroxide | 1.00 |
| ascorbyl palmitate | 0.15 |
| copper acetyl acetonate | 0.02 |
| LIQUID | |
| Product of example 3 | 92.00 |
| Water | 8.00 |

This cement is adhesive to dentin and enamel without further treatment except cleansing with pumice. The mixture has a "work time" during which it can be handled and used of 3.0 minutes and a "set time" of 4.5 minutes. The hardened product has a compressive strength of 149 MPa, a diametral tensile strength of 34.2 MPa, a dentin bond strength in 24 hours of 10.5 MPa and a bond strength to enamel, in 24 hours of 9.0 MPa.

EXAMPLE 15B

Cement 92 grams of oily solution containing OEMA in an excess of HEMA prepared as described in Example 3 is stirred with 8 grams of water to form a liquid formulation. 1 gram of this liquid formulation is mixed with 2 grams of powder product prepared as described in Example 9. This mixture has a work time of 10.0 minutes and a set time of 120 minutes. This mixture reacts to form a cement having a compressive strength of 117 MPa.

EXAMPLE 16

Cement 90 grams of oily solution containing OEMA in an excess of HEMA prepared as described in Example 3 is stirred with 10.0 grams of water to form a liquid formulation. 1 gram of this liquid formulation is mixed with 2 grams of powder product prepared as described in Example 8. This mixture reacts to form a cement. This mixture reacts with a work time of 2.5 minutes and a set time of 2.7 minutes to form a cement having a bond strength to dentin of 7.8 MPa, and a compressive strength of 152 MPa.

As described above the powder products of Examples 7 through 9 are mixed with the corresponding liquid in Examples 10 through 16 at a ratio as shown in the following table to provide cement mixtures. The liquids are prepared with stirring and then mixed with the powders prepared as described in Examples 7 through 9. The resulting cements exhibited mechanical and other properties as shown in Table 2.

tium aluminumfluorosilicate glass to form a one-component precatalyzed product. Upon irradiation of this precatalyzed cement product by visible light from The MAX Lite a polymerized cement product is formed having a bond strength to dentin of 7 MPa, a bond strength to enamel of 12.5 MPa, a diametral tensile strength of 28.6 MPa and a compressive strength of 165.6 MPa.

EXAMPLE 18

25 grams of the oily solution of OPMA in an excess of HPMA prepared as described in Example 4 is stirred with 0.8 grams ethyl dimethylaminobenzoate and 0.2

TABLE 2

| Example Number | SELF CURE CEMENT COMPOSITIONS | | | | | | | | |
|---|---|---|---|---|---|---|---|---|---|
| | 10 | 11 | 12 | 13 | 14 | 15 | 15A | 15B | 16 |
| LIQUID FORMULATION | | | | | | | | | |
| 6FDMA Containing Product of Example 1 (g) | .95 | | | | | | | | |
| BTDMA Containing Product of Example 2 (g) | | .95 | | | | | | | |
| STDMA Containing Product of Example 5 (g) | | | | | .859 | | | | |
| OEMA Containing Product of Example 3 (g) | | | .90 | | | .918 | .92 | .92 | .90 |
| OPMA Containing Product of Example 4 (g) | | | | .95 | | | | | |
| HEMA (g) | | | | | | .061 | | | |
| Water (g) | .05 | .05 | .01 | .05 | .08 | .080 | .08 | .08 | .10 |
| Camphorquinone | | | | | | .002 | | | |
| POWDER FORMULATION | | | | | | | | | |
| Powder of Example 7, (g) | 2.00 | 2.00 | 2.00 | 2.00 | 2.00 | | 2.00 | | |
| Powder of Example 9, (g) | | | | | | 1.80 | | 2.00 | |
| Powder of Example 8, (g) | | | | | | | | | 2.0 |
| POLYMERIZED PRODUCT PROPERTIES | | | | | | | | | |
| Bond to Dentin, MPa | 13.8 | 7.6 | 6.6 | 6.3 | 6.5 | 11.7 | 10.5 | | 7.8 |
| Bond to Enamel, MPa | 9.7 | 10.2 | 9.4 | 18.6 | | | 9.0 | | |
| Bond to Amalgam, MPa | — | — | 17.9 | 20.2 | | | — | | |
| Diametral Tensile MPa | | 28.6 | 32.3 | 27.0 | 26.7 | 37.2 | 34.2 | | |
| Compressive strength MPa | | 116. | 130. | 120. | 139. | 154. | 149 | 117 | 152 |
| Work time, min | 3.0 | 2.3 | 2.5 | 2.5 | 2.5 | 10.0 | 3.0 | 10.0 | 2.5 |
| Set time, min | 4.0 | 3.5 | 3.5 | 3.5 | 3.0 | 120.0 | 4.5 | 120.0 | 2.7 |

One Component Light Cured Cement Filling Material Compositions

In each of Examples 17 through 21 as shown in the Table 3 liquids are formulated containing an acid functional monomer, diluent comonomers, camphorquinone and catalysts and accelerators for polymerization of the polymerizable material. The strontium aluminofluorosilicate glass is added with stirring to form a one-component precatalyzed mixture adapted to be polymerized by irradiation from The MAX Lite as described previously.

EXAMPLE 17

25 grams of the oily solution of OEMA in an excess of HEMA prepared as described in Example 3 is stirred with 0.8 grams ethyl dimethylaminobenzoate and 0.2 grams of camphorquinone to form a liquid solution. This liquid solution is stirred with 74.0 grams of strongrams of camphorquinone to form a liquid solution. This liquid solution is stirred with 74.0 grams of strontium aluminum silicate glass to form a one-component precatalyzed product. Upon irradiation of this precatalyzed cement product by visible light from The MAX Lite a polymerized cement product is formed having a bond strength to dentin of 7.5 MPa, a bond strength to enamel of 13.8 MPa, a diametral tensile strength of 25.8 MPa and a compressive strength of 167.1 MPa.

EXAMPLE 19

25 grams of the solution containing 70% by weight of 6FDMA and 30% by weight HEMA prepared as described in Example 1 is stirred with 0.8 grams 4-ethyl dimethylaminobenzoate and 0.2 grams of camphorquinone to form a liquid solution. This liquid solution is stirred with 74.0 grams of strontium aluminum silicate glass to form a one-component precatalyzed product.

Upon irradiation of this precatalyzed cement product by visible light from The MAX Lite a polymerized cement product is formed having a bond strength to dentin of 10.1 MPa a diametral tensile strength of 20.5 MPa and a compressive strength of 157 MPa.

EXAMPLE 20

8.75 grams of the oily solution of OPMA in an excess of HPMA prepared as described in Example 4 is stirred with 12.5 grams of urethanedimethacrylate (prepared as described in Example 1 of U.S. Pat. No. 4,657,941) 3.75 grams of glycerol dimethacrylate (Rohm Tech. D1108), 0.5 grams of MDEA (methyl diethanolamine) and 0.2 grams of camphorquinone to form a liquid solution. The liquid solution is stirred with 74.0 grams of strontium aluminumfluorosilicate glass to form a one-component precatalyzed product. Upon irradiation of this precatalyzed cement product by visible light from The MAX Lite a polymerized cement product is formed having a bond strength to dentin of 7.9 MPa, a bond strength to enamel of 10.7 MPa, a diametral tensile strength of 27.5 MPa and a compressive strength of 141.5 MPa.

EXAMPLE 21

20.79 grams of the oily solution of OEMA in TEGDMA prepared as described in Example 6 and 2.36 grams TEGDMA are stirred with 0.181 grams 4-ethyl dimethylaminobenzoate and 0.046 grams of camphorquinone to form a liquid solution. This liquid solution is stirred with 76.62 grams of strontium aluminumfluorosilicate glass to form a one-component precatalyzed product. Upon irradiation of this precatalyzed cement product by visible light from The MAX Lite a polymerized cement product is formed having a bond strength to dentin of 4.0 MPa, a bond strength to enamel of 4.7 MPa, a diametral tensile strength of 28.9 MPa and a compressive of 182.6 MPa.

The compositions and physical and mechanical properties of the products described in Examples 17 through 21 are shown in Table 3.

The product of example 2, BTDMA in an excess of HEMA, is strongly orange-yellow colored as prepared. When formulated into a cement according to example 11, and polymerized, the cement has a strong green color which is not practical for use in dental cement compositions, although it exhibits other desirable properties. In contrast, the products of Examples 1, 3, 4 and 5 are light straw colored before polymerization. When formulated into cement compositions, according to Examples 10 and 12 through 20 the products are milky white translucent cements that are suitable for rendering in tooth shades by the addition of pigments.

EXAMPLE 22

Cement 92 grams of oily solution containing OEMA in an excess of HEMA prepared as described in Example 3 is stirred with 5 grams of water to form a liquid formulation. 1.0 gram of this liquid formulation is mixed with 3 grams of powder product prepared as described in Example 7. This mixture reacts to form a cement having soxhlet fluoride release over a period of seven days as follows:

| | SELF ADHESIVE CEMENT | |
|---|---|---|
| Day | Daily Fluoride Release µg F—/gram of composite | Cumulative Fluoride Release µg F—/gram of composite |
| 1 | 1817.28 | 1817.28 |
| 2 | 837.69 | 2654.97 |
| 3 | 525.40 | 3180.37 |
| 4 | 548.22 | 3728.59 |
| 5 | 368.63 | 4697.22 |
| 6 | 351.90 | 4449.12 |
| 7 | 305.46 | 4754.58 |

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

TABLE 3

| COMPOSITIONS OF ONE COMPONENT VLC CEMENTS | | | | | |
|---|---|---|---|---|---|
| Example Number | 17 | 18 | 19 | 20 | 21 |
| LIQUID FORMULATION | | | | | |
| 6FDMA Containing Product of Example 1 (g) | — | — | 25 | | |
| OEMA Containing Product of Example 6 (g) | — | — | | | 20.79 |
| OEMA Containing Product of Example 3 (g) | 25 | — | | | |
| OPMA Containing Product of Example 4 (g) | — | 25 | | 8.75 | |
| UDMA (g) | — | — | — | 12.5 | |
| GLYCEROL DIMETHACRYLATE* (g) | | | | 3.75 | |
| TEGDMA (g) | | | | | 2.36 |
| POWDER FORMULATION | | | | | |
| Sr GLASS (g) | 74.0 | 74.0 | 74.0 | 74.0 | 76.62 |
| EDAB (g) | 0.8 | 0.8 | 0.8 | — | 0.181 |
| CQ (g) | 0.2 | 0.2 | 0.2 | 0.2 | 0.046 |
| MDEA (3) (g) | — | — | | 0.5 | |
| POLYMERIZED PRODUCT PROPERTIES | | | | | |
| B.S. TO DENTIN (MPa) | 7 | 7.5 | 10.1 | 7.9 | 4.0 |
| B.S. TO ENAMEL (MPa) | 12.5 | 13.8 | | 10.7 | 4.7 |
| D.T.S. (MPa) | 28.6 | 25.8 | 20.5 | 27.5 | 28.9 |
| C.S. (MPa) | 165.6 | 167.1 | 157 | 141.5 | 182.6 |

*ROHM TECH D 1108

1. A dental cement composition, comprising:

a cation source and a polymerizable monomer compound of the general formula

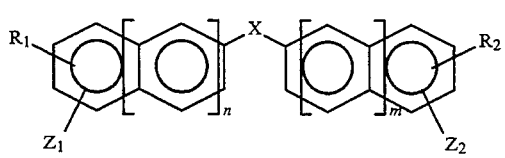

wherein
X, is O, S,

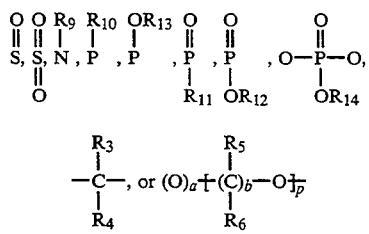

$$-\underset{\underset{R_4}{|}}{\overset{\overset{R_3}{|}}{C}}-, \text{ or } (O)_a\!\!+\!\!(C)_b\!\!-\!\!O\!\!+\!\!_p$$
$$\phantom{-C-,\text{ or }(O)_a\!\!+\!}\underset{R_6}{|}^{R_5}$$

$R_1$ and $R_2$ each independently is a polymerizable unsaturated moiety having from 2 to 13 carbon atoms, $R_3$, $R_4$, $R_5$, and $R_6$ each independently is hydrogen, halogen, alkyl of from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms.

$Z_1$ and $Z_2$ each independently is a moiety including an acid group or a reactive acid derivative, a, m and n each independently is 0 or 1, b and p each independently is an integer from 1 to 10.

2. The composition of claim 1 wherein said cation source comprises ions of calcium, aluminum or strontium.

3. The composition of claim 1 further comprising a diluent comonomer.

4. The composition of claim 2 wherein said cation source further comprises glass-particles.

5. The composition of claim 1 wherein n and m are zero.

6. The composition of claim 5 wherein X is oxygen or

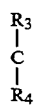

wherein $R_3$ and $R_4$ each independently is a fluorinated methyl moiety.

7. The composition of claim 6 wherein $Z_1$ and $Z_2$ are —COOM wherein M is hydrogen, lithium, ammonium, sodium, potassium, calcium, aluminum or strontium.

8. The composition of claim 1 wherein said cation source comprises a glass filler from which reactive ions of calcium, strontium or alumina are eluted.

9. The composition of claim 1 further comprising a source of fluoride ion.

10. A method of adhering a dental cement to tooth material, comprising:

providing a dental cement, said cement comprising a compound of the general formula

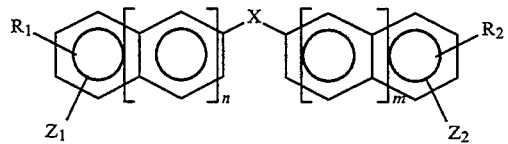

wherein
X, is O, S,

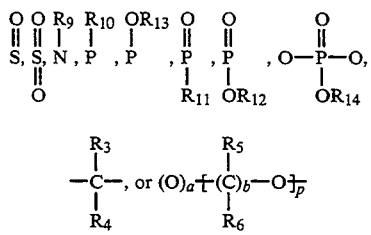

$$-\underset{\underset{R_4}{|}}{\overset{\overset{R_3}{|}}{C}}-, \text{ or } (O)_a\!\!+\!\!(C)_b\!\!-\!\!O\!\!+\!\!_p$$
$$\phantom{-C-,\text{ or }(O)_a\!\!+\!}\underset{R_6}{|}^{R_5}$$

$R_1$ and $R_2$ each independently is a polymerizable unsaturated moiety having from 2 to 13 carbon atoms;

$R_3$, $R_4$, $R_5$, and $R_6$ each independently is hydrogen, halogen, alkyl of from 1 to 10 carbon atoms or halogenated alkyl of from 1 to 10 carbon atoms;

$R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms.

$Z_1$ and $Z_2$ each independently is a moiety including an acid group or a reactive acid derivative;

a, m and n each independently is 0 or 1;

b and p each independently is an integer from 1 to 10; applying said cement to tooth material.

11. The method of claim 10 wherein said applying is without prior treatment of said tooth material, except cleaning to increase adhesion of said cement to said tooth material.

12. The method of claim 10 wherein said cation source comprises ions of calcium, aluminum or strontium.

13. The method of claim 10 further comprising a diluent comonomer.

14. The method of claim 12 wherein said cation source further comprises glass particles.

15. The method of claim 10 wherein n and m are zero.

16. The method of claim 15 wherein X is oxygen

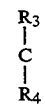

wherein $R_3$ and $R_4$ are fluorinated methyl moieties.

17. The method of claim 16 wherein $Z_1$ and $Z_2$ are —COOM wherein M is hydrogen, ammonium, an alkali metal, alkaline-earth metal, aluminum or strontium.

18. The method of claim 16 wherein M is hydrogen, lithium, ammonium, sodium, potassium, calcium, aluminum or strontium.

19. A dental composition for adhering to tooth material, comprising:

a polymerized dental product formed from a dental cement, said cement comprising a compound of the general formula

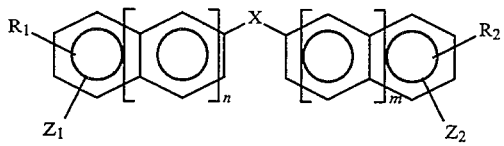

wherein

X, is O, S,

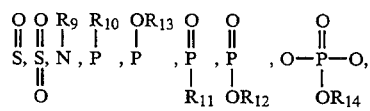

-continued $$-\overset{R_3}{\underset{R_4}{\overset{|}{C}}}-, \text{ or } (O)_a \overset{R_5}{\underset{R_6}{\overset{|}{+(C)_b}}} -O)_p$$

$R_1$ and $R_2$ each independently is a polymerizable unsaturated moiety having from 2 to 13 carbon atoms;

$R_3$, $R_4$, $R_5$, and $R_6$ each independently is hydrogen, halogen, alkyl of from 1 to 10 carbon atoms or halogenated alkyl of from 1 to 10 carbon atoms;

$R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms.

$Z_1$ and $Z_2$ each independently is a moiety including an acid group or a reactive acid derivative;

a, m and n each independently is 0 or 1;

b and p each independently is an integer from 1 to 10.

20. The dental composition of claim 19 wherein said polymerized product is a dental filling material, pit and fissure sealant, luting cement, base or orthodontic cement.

* * * * *